United States Patent [19]
Groh et al.

[11] Patent Number: 5,211,894
[45] Date of Patent: May 18, 1993

[54] SKIN REPLICATION TECHNIQUE

[75] Inventors: David G. Groh, Walker; James D. Ayres, Kentwood, both of Mich.

[73] Assignee: Amway Corporation, Ada, Mich.

[21] Appl. No.: 591,411

[22] Filed: Oct. 9, 1990

[51] Int. Cl.$^5$ .................. B29C 33/40; B29C 39/02
[52] U.S. Cl. .................. 264/40.1; 264/222; 264/225; 264/226; 264/DIG. 30; 425/2; 523/109
[58] Field of Search .............. 264/40.1, 222, 225–227, 264/102, 219, 224, DIG. 30; 249/55; 425/2; 525/222; 524/265, 266, 284; 523/109

[56] References Cited

U.S. PATENT DOCUMENTS

| | | | |
|---|---|---|---|
| 3,082,527 | 3/1963 | Nitsche et al. | 523/109 |
| 3,261,802 | 7/1966 | Bobear | 524/700 |
| 3,696,090 | 10/1972 | Lampe | 264/222 |
| 3,989,790 | 11/1976 | Bruner et al. | 264/225 |
| 4,007,153 | 2/1977 | Smith | 523/109 |
| 4,071,507 | 1/1978 | Schoen | 528/355 |
| 4,116,914 | 9/1978 | Coran et al. | 525/222 |
| 4,144,206 | 3/1979 | Symeon | 524/266 |
| 4,199,825 | 4/1980 | Knoche | 249/55 |
| 4,223,122 | 9/1980 | Cella | 528/30 |
| 4,302,571 | 11/1981 | Arai et al. | 528/32 |
| 4,341,888 | 7/1982 | Razzano | 528/14 |
| 4,389,496 | 6/1983 | Leüsner et al. | 523/109 |
| 4,421,769 | 12/1983 | Dixon et al. | 424/358 |
| 4,559,189 | 12/1985 | Wegener, II | 264/222 |
| 4,568,707 | 2/1986 | Voigt et al. | 523/109 |
| 4,581,347 | 4/1986 | Kumagai et al. | 514/63 |
| 4,609,545 | 9/1986 | Schlossman | 424/63 |
| 4,619,848 | 10/1986 | Knight et al. | 525/222 |
| 4,623,693 | 11/1986 | Inoue et al. | 524/700 |
| 4,657,959 | 4/1987 | Bryan et al. | 264/222 |
| 4,778,832 | 10/1988 | Futami et al. | 523/109 |
| 4,832,978 | 5/1989 | Lesser | 427/2 |
| 4,837,274 | 6/1989 | Kawakubo et al. | 525/100 |
| 4,882,162 | 11/1989 | Ikada et al. | 424/444 |

OTHER PUBLICATIONS

Makki et al, "A Quantitative Method for the Assessment of the Microtopography of Human Skin" Acta Dermatovener (Stockholm) (1979) pp. 285–291.

Barbenel et al. "The Variability of Skin Surface Contours" Annals of Biomedical Engineering, vol. 8, (1980), pp. 175–182.

Mignot et al. "Microtopographical Analysis of Human Skin Surface" Bioeng Skin (1985) pp. 101–110.

Joan Sampson "A Method of Replicating Dry or Moist Surfaces for Examination by Light Microscopy" (Aug. 1961), pp. 932–933, Nature.

(List continued on next page.)

Primary Examiner—Jay H. Woo
Assistant Examiner—James P. Mackey
Attorney, Agent, or Firm—Michael A. Mohr

[57] ABSTRACT

The invention provides a composition and a method for studying skin surface areas with simplified magnifying devices by making a replication of the skin surface area while minimizing irritation to the subject's skin, cracking of the replicas, surface artifacts, and air bubbles in the replicas. The method entails preparing a negative skin surface replica composition by mixing a silicone polysiloxane base and a biocompatible surface tension modifying agent. The mixture is placed in a vacuum desiccator to remove air bubbles and thereafter a curing agent is added to the mixture. An adhesive collar is placed on the subject's skin, which collar surrounds the surface area to be replicated, and thereafter the composition is applied to the skin surface area and the adhesive collar and allowed to dry. The negative skin surface casting is removed from the skin area and is then placed skin side up in a mold cup. A positive liquid skin surface replica composition comprising a polyethylene, a polyethylene copolymer and a low micron pigment blend is prepared and is heated. The positive replica composition is then poured into the mold cup until the negative casting is covered. The mold cup is centrifuged, cooled to room temperature and thereafter the negative and positive skin surface replica castings are separated and studied.

74 Claims, 5 Drawing Sheets

OTHER PUBLICATIONS

Goldman et al. "Replica Microscopy and Scanning Electron Microscopy of Laser Impacts on the Skin" (1969), pp. 18-23, vol. 52, No. 1. J. Inv. Derm.

Bernstein and Jones "Skin Replication Procedure for the Scanning Electron Microscope" Science (1969), pp. 166, 253.

Kairnen and Kaszynski "Scanning electron microscopy of skin replicas showing demodectic infestation of the pilosebaceous follicle" Journal of Cutaneous Pathology (1984), pp. 103-106, vol. 11.

Kuokkanen "Replica Reflection of Normal Skin and of Skin with Disturbed Keratinization" Acta Dermatovener (Stockholm) (1972) pp. 52:205-210.

Barnes "Techniques for the replication of skin surfaces" British Journal of Dermatology (1973), pp. 277-283.

Garber and Nightingale "Characterizing Cosmetic Effects and Skin Morphology by Scanning Electron Microscopy" J. Soc. Cosmet. Chem. (1976), pp. 509-531.

Pameijer "Replication Techniques with New Dental Impression Materials in Combination with Different Negative Impression Materials" Scanning Electron Microscopy (1979), pp. 571-574.

Ryan et al. "A replica technique for the evaluation of human skin by scanning electron microscopy" Journal of Cutaneous Pathology (1983), pp. 262-276.

SKIN REPLICATION TECHNIQUE

FIELD OF THE INVENTION

The present invention relates generally to a method and a composition used to replicate surface areas for purposes of evaluating such surface areas. More particularly, the present invention relates to a skin replication method and composition used for skin surface evaluation which uses a composition comprised of a silicone polysiloxane base, a biocompatible surface tension modifying agent and a curing catalyst to form a negative skin surface replica casting and a composition comprised of a pigment, polyethylene and polyethylene copolymer to obtain a positive skin surface replica casting from the negative skin surface replica casting.

BACKGROUND OF THE INVENTION

Various skin replication methods have been used by researchers for years to study the external surface of the skin without the use of biopsies. These methods not only allow for the in vivo study of skin surfaces, but permit comparative observations to be made of topography of the skin prior to and after the application of various substances such as lotions, cosmetics, and medicinal mixtures.

Methods of studying skin surfaces by skin replication include the technique of making a negative impression of the skin surface at the test site and thereafter studying the negative impression or negative replica through the use of various types of magnifying equipment such as scanning electron microscopy (SEM). One method which uses this negative replica technique for studying skin surfaces involves the steps of placing a negative replica composition on the skin, curing the composition, removing the composition and studying the result by taking a picture of the negative replica while the replica is irradiated with light and observing the resultant pictures from the reverse direction.

Another method of studying skin surfaces entails the technique of making a negative replica of the skin surface test site and thereafter forming a positive replica from the negative casting. The positive replica is then evaluated through the use of some type of special magnifying equipment such as SEM. The methods and compositions used for forming the positive skin replica are varied. In one related art method, a negative replica of the test surface is made by covering the test surface with a silicone base material containing a catalyst and thereafter removing the polymerized replica. A mold held together by clamps is used to procure the positive replica. It is suggested that either polyethylene beads or a liquid cured Spurr imbedding resin be used to make the positive replica. Other methods of studying skin surfaces are disclosed in the references cited in applicant's Information Disclosure Statement.

While the related art methodologies appear to be effective in evaluation of skin surfaces, these methods have problems in that the compositions used to cast the negative replicas often prove to be an irritant to the subject's skin. Further, these methods often produce cracking of either the negative or positive replica and surface artifacts in the negative or positive replica caused by trapped air or by poor processing and selection of replicating materials. This cracking of either of the replicas and surface artifacts can introduce error in the researcher's results. Also, materials used to make the skin replicas in some related art methods produce a clear or white surface area which can present problems when attempting to visually evaluate and/or photograph such replicas. Additionally, in many instances in order to obtain accurate results, related art methods can only be performed with any degree of accuracy by technicians skilled in the art and with the use of special lab equipment. Further, the evaluation of the replicas must be done with special lighting or special diagnostic and magnifying equipment such as SEM, Image Analysis or Profilometry.

SUMMARY OF THE INVENTION

According to the present invention, these and other problems in the related art are solved by the provision of a composition and method for use in obtaining a surface replica which can be evaluated by simple magnifying means. The composition used in casting the negative surface replica comprises a silicone polysiloxane base, a surface tension modifying agent and a curing agent. In one embodiment of the invention the surface tension modifying agent is biocompatible which, when being used to test skin surfaces, has the advantages of being a non-irritant to the subject's skin and harmless with respect to dermal toxicology. In the preferred embodiment of the invention the surface tension modifying agent is chemically compatible with the base which aids in significantly reducing surface artifacts which are found in the related art. The positive surface replica casting composition comprises a blend of polyethylene, a polyethylene copolymer and a pigment. The polyethylene and polyethylene copolymer in the blend have advantages over the related art in that the addition of these constituents helps to prevent cracking of the positive surface replica casting. Further, the polyethylene copolymer serves to suspend the pigment throughout the positive surface replica casting thereby avoiding problems in the related art of the pigment grouping in one area of the casting only. The pigment blend aids in the observation or photography of the finished positive surface replica casting and avoids the need for special lighting in the observation of the finished casting.

According to another aspect of the present invention, there is also provided a composition and method for examining the surface appearance of skin and changes in the surface appearance of skin after the application of substances such as lotions, cosmetics and medicinal mixtures, which is designed for use by any researcher, whether skilled or unskilled in the art, in any standard laboratory. As described in the preferred embodiment, standard laboratory equipment may be used, which has the advantage of giving the researcher the ability to produce and more effectively evaluate positive skin surface replica castings with inexpensive and readily available laboratory equipment.

The method of the invention comprises formation of a positive surface replica casting from the casting of a negative surface replica comprising the steps of: (a) preparing the negative surface replica composition; (b) placing the negative surface replica composition in a vacuum desiccator to remove trapped air; (c) positioning the surface area to be replicated horizontally; (d) curing the negative surface replica composition; (e) applying the negative surface replica composition to the surface area to be replicated; (f) allowing the negative surface replica composition to dry; (g) removing the dried negative surface replica casting from the surface area; (h) placing the negative surface replica casting surface side up in the bottom of a mold cup; (i) preparing a liquid positive surface replica composition; (j) heating the positive surface replica composition to 260° F.-300° F. which pour temperature has the advantage over related art as at this temperature viscosity is reduced and reduction of artifacts in the positive surface replica casting is facilitated; (k) covering the negative surface replica casting which has been placed in the mold cup with the liquid positive surface replica composition; (l) centrifuging the filled mold cup which centrifuging further eliminates surface pitting found in the related art of making surface replicas; (m) removing the connected positive and negative surface replica castings from the mold cup; (n) separating the negative and positive surface replica castings at their interface; (o) viewing the positive surface replica casting under a stereo microscope or other magnifying means for close examination of details or using microphotography equipment to record the results.

DESCRIPTION OF THE PREFERRED EMBODIMENTS

According to the present invention, the surface of the skin is evaluated by making a negative skin surface replica casting and thereafter forming a positive skin surface replica casting from the negative skin surface replica casting which will be suitable for visual and/or mechanical evaluation. The method requires the following standard laboratory equipment: standard laboratory glassware, hot plate, centrifuge (IEC HNS II with 30 mm catch tubes), 2 spacers for centrifuge tubes (2 inches long), adhesive collars (Biochem International Cat. No. 2074), Binocular Microscope (Fisher, 15× eye piece, 1× & 3×), and mold cups (1" ID, Leco Corporation, Part No. 810-990-012).

The negative skin surface replica composition is comprised of a silicone polysiloxane base, a curing catalyst and a biocompatible surface tension modifying agent.

Figure 1:
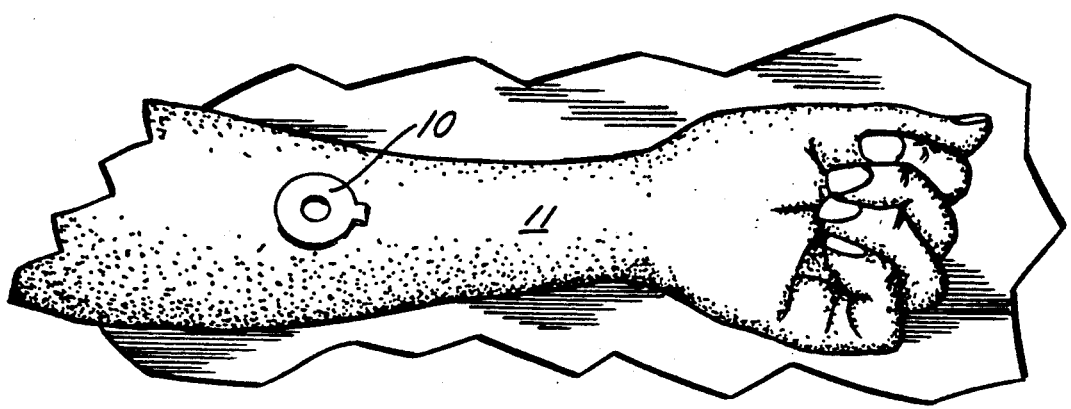
FIG. 1 illustrates the step of placing an adhesive collar over the surface area to be replicated.

The base used is any room temperature vulcanizing diorganopolysiloxane, preferably dimethylpolysiloxane. The preferred silicone polysiloxane base is RTV-11 and is commercially available from General Electric. Examples of the biocompatible surface tension modifying agent are silicone fluids such as dimethicone and cyclomethicone and surfactant and non-ionic emulsifier mixtures. The preferred biocompatible surface tension modifying agent is a surfactant and non-ionic emulsifier mixture in the ratio of 95-55/5-45 by weight and is used to aid in the elimination of air bubbles incorporated in the silicone polysiloxane base such as are shown at FIG. 1, Number 10. The preferred surfactant in the mixture is polyether modified polysiloxane and specifically the preferred mixture is a blend of cetyl dimethicone copolyol and polyglyceryl-4-isosterate and hexyl laurate in the ratio of 100-50/0-40/0-10 percent respectively, although other combinations of polyether modified polysiloxane and non-ionic organic emulsifiers can be used such as a blend of cetyl dimethicone, polyglyceryl-3-oleate and hexyl laurate. A comparable blend of the preferred biocompatible surface tension modifying agent is commercially available from Goldschmidt Chemicals as Abil WE09. The preferred silicone polysiloxane base and preferred biocompatible surface tension modifying agent are mixed in the range of 99.90/95.00% to 0.10/5.00% and preferably in the ratio of 99.25% to 0.75% based on weight with a 100 gram batch minimum, although other ratios can be used. This base is mixed thoroughly with the surface tension modifying agent and is then placed in a vacuum desiccator in the range of 5-15 minutes to remove trapped air. Prior to application at the test site, a curing catalyst is added to the base and surface tension modifying agent mixture, the curing catalyst preferably being a metallic salt of carboxylic acid. Stannous tin octoate (STO) is the preferred metallic salt and is added in the range of 2.0% to 5.0% by weight of the total weight of the base and modifying agent mixture and preferably at 2.5% STO of the total weight of the base and modifying agent mixture. The curing catalyst is carefully mixed for approximately 8-15 seconds, carefully avoiding the entrapment of air during mixing.

The positive skin replica composition comprises a polyethylene, a polyethylene copolymer and a low micron pigment blend. The preferred polyethylene is provided with a molecular weight in a range of greater than 1,100 but less than 5,000. The preferred polyethylene is AC-617A, commercially available from Allied Chemical.

Examples of polyethylene copolymer which can be used are ethylene-acrylic acid copolymer, ethylene-polyvinyl acetate copolymer, ethylene-methyl methacrylate copolymer and ethylene-vinyl acetate copolymer, with the preferred polyethylene copolymer being ethylene-vinyl acetate copolymer provided with a molecular weight in a range of greater than 2,000 but less than 8,000. The polyethylene and polyethylene copolymer are mixed in the range of 5/95% to 95/5% by weight respectively and preferably mixed in the ratio of 75% to 25% by weight respectively. A low micron pigment blend is added to the polyethylene/polyethelene copolymer blend. Examples of pigment which can be used are black iron oxide, red iron oxide, yellow iron oxide, brown iron oxide, ultramarine blue, or chromium oxide green, although other colored pigments can be used. The low micron pigment blend can be made by milling any one or a combination of the pigments with talc, castor oil or titanium dioxide. The preferred low micron pigment blend is comprised of 50% black iron oxide pigment milled into castor oil with the preferred black iron oxide pigment being commercially available as #7053 from Clark Colors, Inc. The low micron black iron oxide pigment blend is added in the range of 0.25% to 10% by weight of the total weight of the polyethylene/polyethylene copolymer blend and preferably at 1.5% of the total weight of the polyethylene/polyethylene copolymer blend. The positive skin surface replica composition is heated to between 260°-300° F., with 260° F. being the optimum pour temperature of the composition to avoid surface artifacts.

With reference now to the figures and in particular to FIG. 1, an adhesive collar 10 is positioned on the skin surface 11 to be replicated and the skin surface 11 is placed horizontally. Any type of adhesive collar 10 having an inner and outer ring can be used with the preferred adhesive collar commercially available from Biochem International, Catalog No. 2074. If a test of the skin surface area is being performed to determine effects of application of certain substances, a before and after positive skin surface replica casting can be made for comparison purposes. In any such test, it will be critical to the validity of the experiment that the exact same skin surface area be tested both before and after application of the substance. This can be assured by marking the skin or outlining onto the skin the shape of the collar with a "skin scribe" surgical pen or other marker and simply repeating the skin replication method at the same location after the test procedure is completed.

Figure 2:
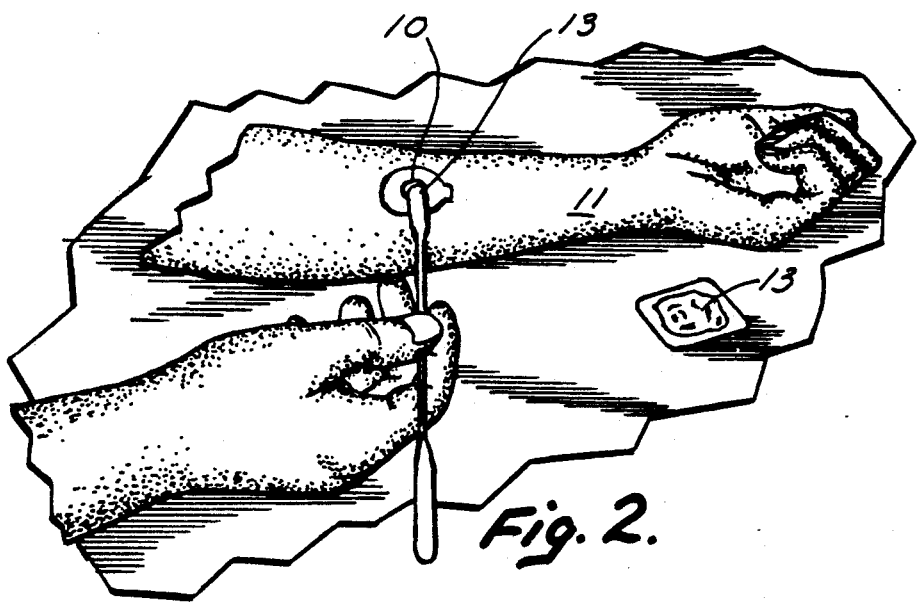
FIG. 2 illustrates the step of applying the negative surface replica composition to the surface area to be replicated and to the adhesive collar.
Figure 3:
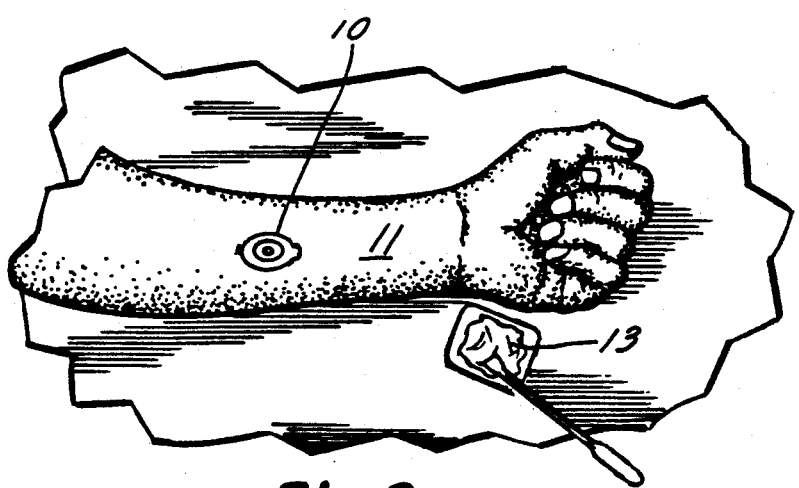
FIG. 3 illustrates the step of curing the negative surface replica composition.
Figure 4:
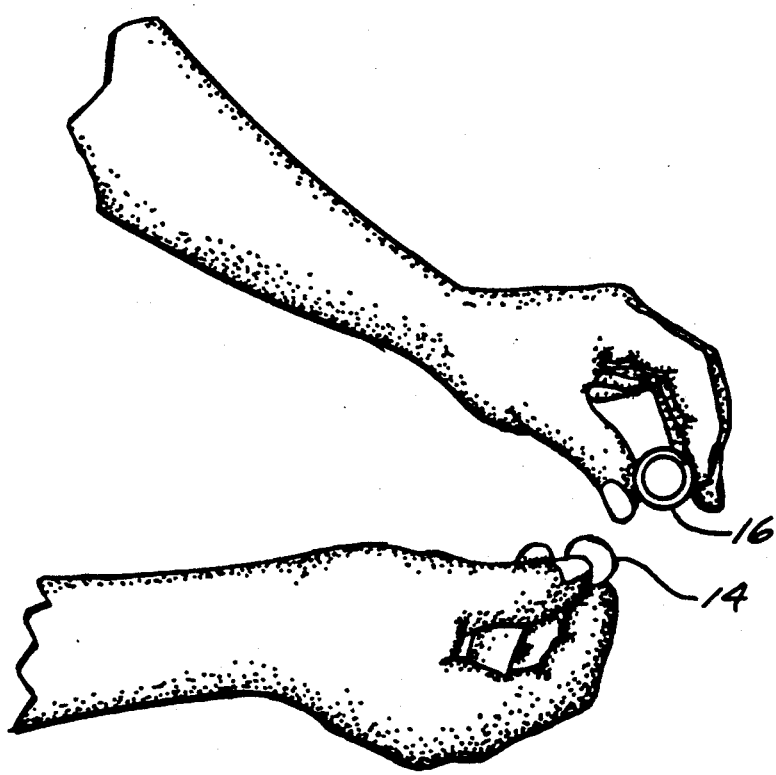
FIG. 4 illustrates the step of placing the negative surface replica casting replicated surface side up in the bottom of a container.
Figure 5:
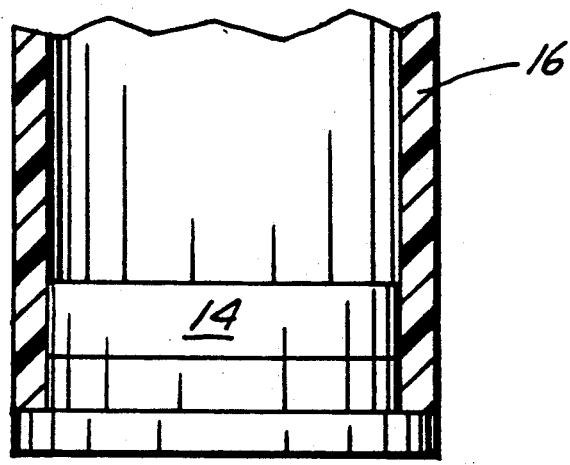
FIG. 5 is an elevational view, partially in section, showing the negative surface replica casting in place at the bottom of the container.
Figure 6:
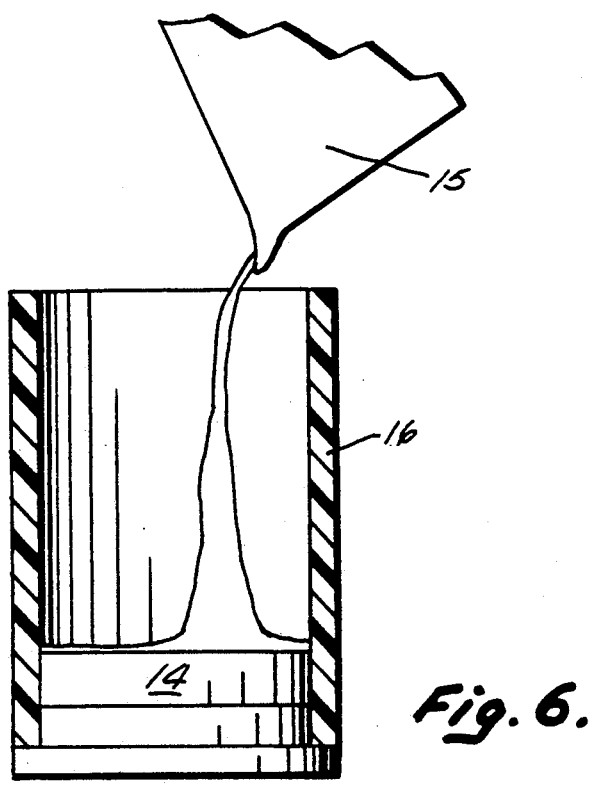
FIG. 6 illustrates the step of covering the negative surface replica casting with the heated liquid positive surface replica composition showing an elevational view of the container partially in section.
Figure 7:
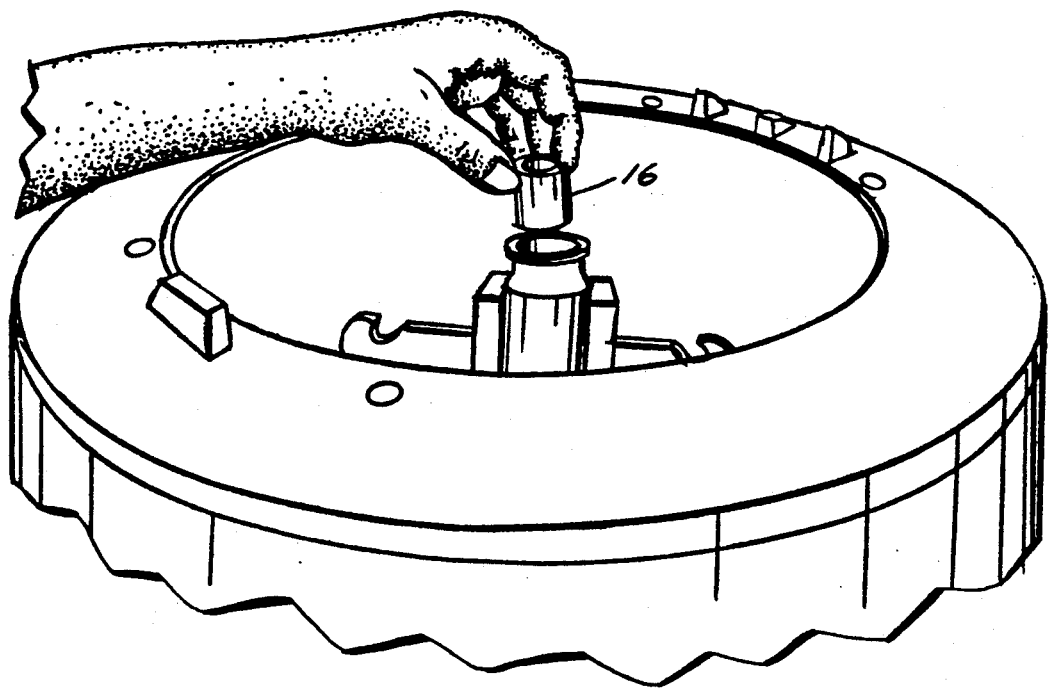
FIG. 7 illustrates the step of placing the container in a centrifuge and thereafter centrifuging the container.
Figure 8:
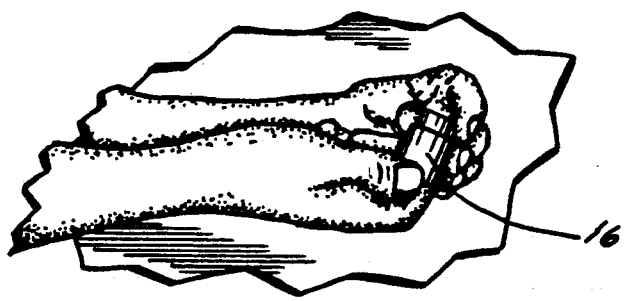
FIGS. 8, 9 and 10 illustrate the step of separating the connected positive and negative surface castings at the interface.
Figure 9:
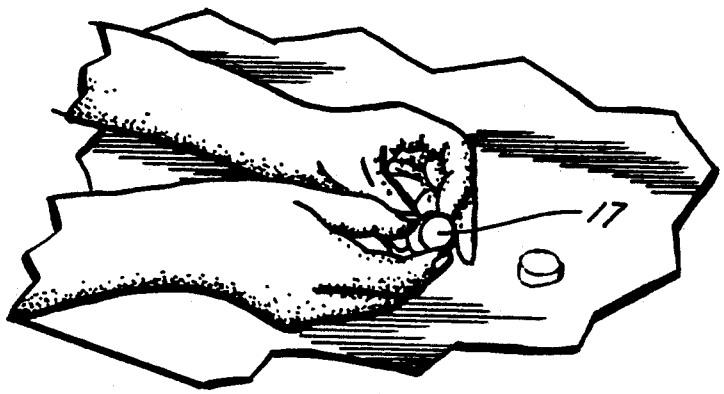
Figure 10:
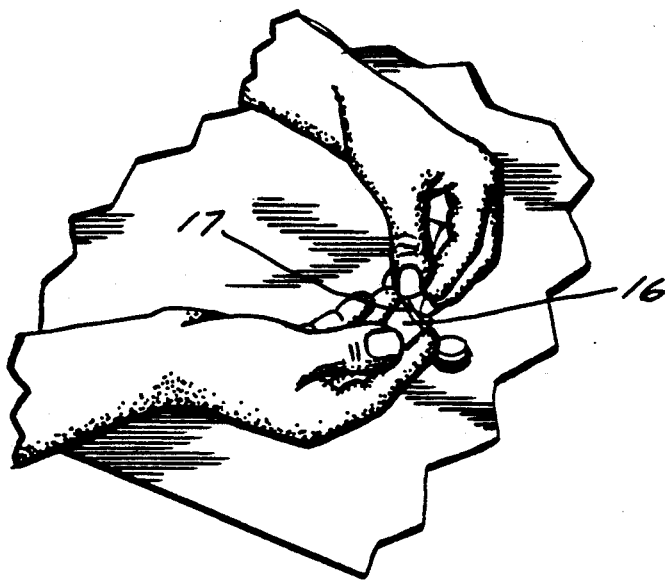
Figure 11:
FIG. 11 illustrates the step of observing the negative and positive surface replica castings.
Figure 12:
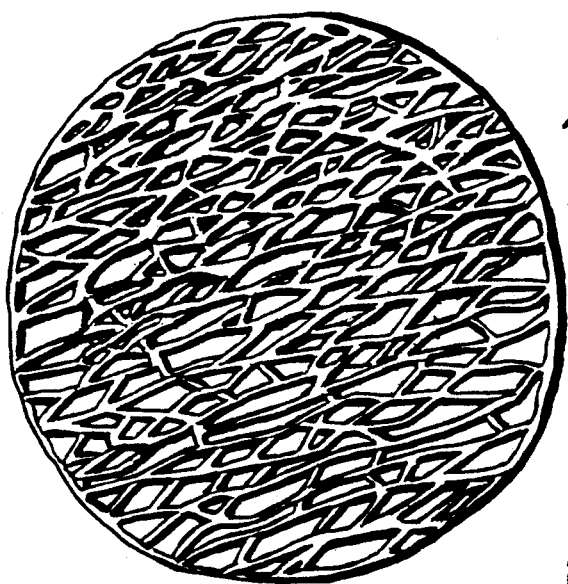
FIG. 12 is representative of the negative surface replica casting.
Figure 13:
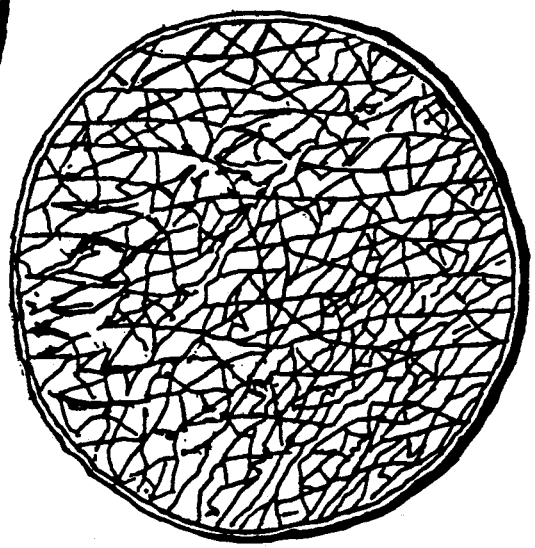
FIG. 13 is representative of the positive surface replica casting.

With reference now to FIGS. 2 and 3, negative skin surface replica composition 13 is then placed in a layer ranging from 2-3 mm on the skin surface area 11 to be replicated. The replication area should be surrounded by the inner ring of the adhesive collar 10. The composition 13 is spread both on the inner ring and outer ring of the adhesive collar 10 and the skin surface 11 to be replicated to provide for easy removal of a dried negative skin surface replica casting shown generally at 14 in FIG. 12. The composition 13 is allowed to dry for approximately 2-3 minutes. Once the composition is dry, the adhesive collar 10 is removed from the skin surface area 11 and thereafter the inner ring of the adhesive collar 10, which is connected to the negative skin surface casting 14, is separated from the outer ring of the adhesive collar 11. With reference now to FIGS. 4-13, a one-inch mold cup 16 is coated, preferably by spraying, with a mold release agent and allowed to dry. The preferred mold release agent is a mixture of ethanol and dimethicone in the ratio of 95% ethanol to 5% dimethicone, respectively. The negative skin surface replica casting 14, which is made from the negative skin surface composition 13, is placed replicated surface side up in the bottom of the coated mold cup 16 and thereafter covered with pre-heated positive skin surface replica composition 15. With particular reference to FIG. 7, the filled mold cup 16 is then centrifuged at 2,000-6,000 rpm, preferably at 4,000 rpm for 1-2 minutes, thereafter removed from the centrifuge and allowed to cool to room temperature. With reference to FIGS. 8, 9 and 10, the connected positive and negative skin surface replica castings are removed from the mold cup and a positive skin surface replica casting, shown generally at 17 in FIG. 13, is separated from negative skin surface casting 14 at the interface. The positive skin surface replica casting 17, which has been made from the positive skin surface replica composition 15, can then be examined under normal lighting conditions with simplified magnifying means such as a stereo microscope or more complex magnifying means such as SEM.

EXAMPLES

The present invention will be explained in the following illustrative examples, but is not limited by them.

NEGATIVE SKIN SURFACE REPLICA—COMPARATIVE EXAMPLES

EXAMPLE 1

A negative silicone impression was taken from the lower forearm of a human subject via the following method:

An adhesive collar "Biochem International Cat. No. 2074" was placed on the desired site. The adhesive collar was then outlined with a purple surgical pen "Skin Scribe" so that any following negative impressions could be obtained from the exact same location for before and after comparison. Next, 0.75% by weight of a surfactant "Zonyl FSN, Du Pont" was mixed with 99.25% by weight of a room temperature vulcanizing diorganopolysiloxane "RTV-11, General Electric". This mixture was then placed in a vacuum desiccator for 5 minutes until all of the air bubbles, trapped air from mixing, had dissipated. Two grams of the silicone/surfactant mixture was then combined with 3.0% by weight of a curing catalyst "STO, Stannous Tin Octoate, General Electric" and mixed for 15 seconds being careful not to entrap any air. After the 15 second mix time, this material was then applied over the surface of the adhesive collar and the skin. Upon curing, approximately 90 seconds, the negative silicone impression/adhesive collar was gently peeled away from the surface of the skin. The outer ring of the adhesive collar was removed and the center silicone negative skin impression was evaluated for surface artifacts (i.e. defects, imperfections, etc.) by application of a pigmented coating. The highly reflective surface of the silicone negative can be evaluated for artifacts because the pigment fills the voids caused by surface defects thus making them apparent under the microscope.

EXAMPLE 2

A negative skin surface replica casting was prepared as described in Example 1 with the exception that the surfactant in Example 1 (Zonyl FSN) was replaced with a polyether modified polysiloxane surfactant (Abil WE-09, Goldschmidt AG).

Example 3 (Comparative Example)

A negative skin surface replica casting was prepared as described in Example 1 with the exception that no surfactant was used to modify the RTV-11.

A comparison of Examples 1, 2 and 3 shows that the negative casting without surfactant, Example 3, had a number of surface artifacts compared to Example 1 and 2. Example 1 shows a decrease in surface artifacts compared to Example 3, while surface artifacts had been virtually eliminated in Example 2 with the addition of a polyether modified polysiloxane surfactant.

POSITIVE SKIN SURFACE REPLICA—COMPARATIVE EXAMPLES

EXAMPLE 4

A positive polyethylene skin replica or "polyethylene positive" was prepared via the following method:

50% by weight of polyethylene "AC-617A, Allied Chemical" was combined with ethylene vinyl acetate copolymer "AC-400, Allied Chemical". To this blend 1.5% of a black iron oxide premix was added and mixed in with a flat blade spatula. The pigment premix consists of 50% by weight of a black iron oxide ground into castor oil on a roller mill. The pigmented polyethylene blend was placed on a lab hot plate and heated to 270° F. with occasional mixing. It is critical that the pour temperature of the polyethylene blend be 260° F. or above so that surface artifacts will not be introduced during the casting of the positive replica. The inside of a one-inch diameter mold cup "Leco Corporation" was coated with a mold release agent consisting of 5% by weight of a 1000 Cst silicone fluid combined with ethanol. The treated mold cup was allowed to dry and the silicone negative obtained in Example 2 was placed in the bottom, skin surface side up. The mold cup was then filled half way with the molten pigmented polyethylene blend and immediately placed in a centrifuge at 4000 RPM for one minute. After centrifuging, the mold cup was cooled to room temperature and the bottom removed. The polyethylene positive/silicone negative was pushed out through the bottom of the mold cup by pressing on the top of the mold. The silicone negative was then carefully separated from the surface of the polyethylene positive by removing any excess casting material and peeling back the silicone negative. The finished polyethylene positive was then evaluated for surface artifacts and reproduction detail.

EXAMPLE 5

A positive casting was prepared as described in Example 4 with the exception that the polyethylene/polyethylene copolymer blend consisted of 75% by weight of polyethylene (AC-617A) with 25% by weight of ethylene vinyl acetate copolymer AC-400 (sample 5).

Example 6 (Comparative Example)

A positive casting was prepared as in Example 4 with the exception that no pigment was added to the polyethylene/polyethylene copolymer blend.

A comparison of the three positive skin surface replica castings reveals the ease with which pigmented positive castings, Examples 4 & 5, can be evaluated compared to a non-pigmented positive casting, Example 6. Example 4 shows good pigment dispersion and acceptable surface detail, while Example 5 shows good pigment dispersion with an increase in overall surface detail. This increase in surface detail can be attributed to the decrease in viscosity when using a 75/25 polyethylene blend described in Example 5.

The above description is that of the preferred embodiment only. Modifications to the invention will occur to those who make and use the invention. It is conceivable that this composition and method could be used to test any non-pourous surface such as floors, can finishes, jewelry and glass. The true scope and spirit of the invention is to be determined by reference to the appended claims. It is desired to include within the present invention all such modifications of the invention that come within the proper scope of the appended claims.

What is claimed is:

1. A method of studying surface areas by making a positive surface replica casting from a negative surface replica casting comprising the steps of:

mixing a silicone polysiloxane base comprising a room temperature vulcanizing diorganopolysiloxane and a surface tension modifying agent;

removing air bubbles from the silicone polysiloxane base and surface tension modifying agent mixture;

forming a negative surface replica composition comprising a curing catalyst and the silicone polysiloxane base and surface tension modifying agent mixture;

positioning an adhesive collar over the surface area to be replicated;

applying the negative surface replica composition to the surface area to be replicated and to the adhesive collar;

curing the negative surface replicate composition at 25° C. for two minutes;

forming a negative surface replica casting from the cured negative surface replica composition;

removing the adhesive collar and the negative surface replica casting from the surface area;

separating the adhesive collar from the negative surface replica casting;

placing the negative surface replica casting replicated surface side up in the bottom of a container;

forming a liquid positive surface replica composition comprising a polyethylene, a polyethylene copolymer and a pigment;

heating the liquid positive surface replica composition;

covering the negative surface replica casting with the heated liquid positive surface replica composition;

centrifuging the container;

cooling the container;

forming a positive surface replica casting from the negative surface replica casting and from the cooled liquid surface replica composition;

separating a connected positive and negative surface castings at the interface; and observing the negative and positive surface replica castings.

2. The method of claim 1 further comprising the step of positioning the surface area to be replicated horizontally.

3. The method of claim 1 further comprising the step of removing air bubbles from the silicone polysiloxane base and surface tension modifying agent mixture by placing said mixture in a vacuum desiccator.

4. The method of claim 3 further comprising the step of placing the silicone polysiloxane base and surface tension modifying agent mixture in a vacuum desiccator for 5–15 minutes.

5. The method of claim 1 wherein the container is a mold cup.

6. The method of claim 5 further comprising the step of coating the mold cup with a mold release agent.

7. The method of claim 1 further comprising the step of removing the connected positive and negative surface castings from the container.

8. The method of claim 1 further comprising the step of observing the surface replica castings through a magnifying device.

9. The method of claim 1 wherein the room temperature vulcanizing diorganopolysiloxane is dimethylpolysiloxane.

10. The method of claim 1 wherein the polyethylene has a molecular weight ranging from 1,100 to 5,000.

11. The method of claim 1 wherein the polyethylene copolymer is selected from the group consisting of ethylene-acrylic acid copolymer, ethylene-polyvinyl acetate copolymer, ethylene-methyl methacrylate copolymer and ethylene-vinyl acetate copolymer.

12. The method of claim 1 wherein the polyethylene copolymer is ethylene-vinyl acetate copolymer.

13. The method of claim 1 wherein the polyethylene copolymer has a molecular weight ranging from 2,000 to 8,000.

14. The method of claim 1 further comprising the step of mixing the polyethylene and polyethylene copolymer in the range of 5-95/95-5% by weight respectively.

15. The method of claim 1 further comprising the step of mixing the polyethylene and polyethylene copolymer in the range of 75% to 25% by weight respectively.

16. The method of claim 1 further comprising the step of milling the pigment into a low micron blend.

17. The method of claim 16 further comprising the step of milling castor oil and an iron oxide pigment selected from the group consisting of red iron oxide, yellow iron oxide, black iron oxide and brown iron oxide into a low micron blend.

18. The method of claim 16 further comprising the step of milling 50% black iron oxide pigment and castor oil into a low micron pigment blend.

19. The method of claim 16 further comprising the step of milling ultra marine blue pigment and castor oil into a low micron pigment blend.

20. The method of claim 16 further comprising the step of milling chromium oxide green pigment and castor oil into a low micron pigment blend.

21. The method of claim 16 further comprising the step of milling talc and an iron oxide pigment selected from the group consisting of red iron oxide, yellow iron oxide, black iron oxide and brown iron oxide into a low micron pigment blend.

22. The method of claim 16 further comprising the step of milling titanium dioxide and an iron oxide pigment selected from the group consisting of red iron oxide, yellow iron oxide, black iron oxide and brown iron oxide into a low micron pigment blend.

23. The method of claim 16 further comprising the step of milling chromium oxide green pigment and talc into a low micron pigment blend.

24. The method of claim 16 further comprising the step of milling chromium oxide green pigment and titanium dioxide into a low micron pigment blend.

25. The method of claim 16 further comprising the step of milling ultra marine blue pigment and talc into a low micron pigment blend.

26. The method of claim 16 further comprising the step of milling ultra marine blue pigment and titanium dioxide into a low micron pigment blend.

27. The method of claim 1 wherein the pigment comprises from 0.25% to 10% by weight of the total weight of the positive surface replica composition.

28. The method of claim 1 wherein the pigment comprises 1.5% by weight of the total weight of the positive surface replica composition.

29. The method of claim 16 wherein the low micron pigment blend comprises 1.5% by weight of the total weight of the positive surface replica composition.

30. The method of claim 16 wherein the low micron pigment blend comprises from 0.25% to 10% by weight of the total weight of the positive surface replica composition.

31. The method of claim 1 further comprising the step of heating the positive surface replica composition in a range of 260° F.-300° F.

32. The method of claim 1 further comprising the step of heating the positive surface replica composition to 260° F.

33. A method of studying changes in the skin surface caused by substances applied to the skin by making a before and after positive skin surface replica casting of the skin surface test area comprising the steps of:
mixing a silicone polysiloxane base comprising a room temperature vulcanizing diorganopolysiloxane and a biocompatible surface tension modifying agent;
removing air bubbles from the silicone polysiloxane base and the biocompatible surface tension modifying agent;
marking the skin surface test area;
forming a negative skin surface replica composition comprising a curing catalyst and the silicone polysiloxane base and the biocompatible surface tension modifying agent mixture;
applying the negative skin surface replica composition to the skin surface area to be replicated;
curing the negative skin surface replica composition at 25° C. for two minutes;
forming a negative surface replica casting from the cured negative surface replica composition;
removing the negative skin surface replica casting from the skin surface area;
placing the negative skin surface replica casting replicated surface side up in a container;
forming a positive skin surface replica composition comprising a polyethylene, a polyethylene copolymer and a pigment;
heating the positive skin surface replica composition;
covering the negative skin surface replica casting with the heated positive skin surface replica composition;
centrifuging the container;
cooling the container;
forming a positive surface replica casting from the negative surface replica casting and the cooled liquid surface replica composition;
separating a connected positive and negative skin surface replica castings at the interface;
applying a test substance on the skin surface test area;
preparing a second negative skin surface replica casting of the test area;
preparing a second positive skin surface replica casting of the test area; and
comparing the first and second positive skin surface replica castings.

34. The method of claim 33 further comprising the step of positioning an adhesive collar over the skin surface area to be tested.

35. The method of claim 34 further comprising the step of applying the negative skin surface replica composition to the skin surface area to be replicated and to an inner and an outer ring of the adhesive collar.

36. The method of claim 35 further comprising the step of removing a negative skin surface replica casting and the adhesive collar from the skin surface area.

37. The method of claim 36 further comprising the step of separating the negative skin surface replica casting from the outer ring of the adhesive collar.

38. The method of claim 33 further comprising the step of cooling the container to room temperature.

39. The method of claim 33 further comprising the step of comparing the first and second positive skin surface replica castings through a magnifying device.

40. The method of claim 33 wherein the biocompatible surface tension modifying agent comprises a mixture of a surfactant and at least one non-ionic emulsifier.

41. The method of claim 33 further comprising the step of mixing the curing catalyst and the silicone polysiloxane base and biocompatible surface tension modifying agent for 8-15 seconds.

42. The method of claim 40 wherein the surfactant is a polyether modified polysiloxane.

43. The method of claim 40 further comprising the step of mixing the surfactant and at least one non-ionic emulsifier in the ratio of 95-55/5-45% by weight respectively.

44. A method of studying changes in the skin surface caused by substances applied to the skin by making a before and after positive skin surface replica casting of the skin surface test area comprising the steps of:
mixing a silicone polysiloxane base and a biocompatible surface tension modifying agent;
removing air bubbles from the silicone polysiloxane base and the biocompatible surface tension modifying agent;
marking the skin surface test area;
forming a negative skin surface replica composition comprising a curing catalyst and the silicone polysiloxane base and the biocompatible surface tension modifying agent mixture;
applying the negative skin surface replica composition to the skin surface area to be replicated;
curing the negative skin surface replica composition;
forming a negative surface replica casting from the cured negative surface replica composition;
removing the negative skin surface replica casting from the skin surface area;
placing the negative skin surface replica casting replicated surface side up in a container;
forming a positive skin surface replica composition comprising a polyethylene, a polyethylene copolymer and a pigment;
heating the positive skin surface replica composition;
covering the negative skin surface replica casting with the heated positive skin surface replica composition;
centrifuging the container;
cooling the container;
forming a positive surface replica casting from the negative surface replica casting and the cooled liquid surface replica composition;
separating a connected positive and negative skin surface replica castings at the interface;
applying a test substance on the skin surface test area;
preparing a second negative skin surface replica casting of the test area;
preparing a second positive skin surface replica casting of the test area;
comparing the first and second positive skin surface replica castings;
wherein the biocompatible surface tension modifying agent comprises a mixture of a surfactant and at least one non-ionic emulsifier; and
wherein the surfactant and at least one non-ionic emulsifier mixture comprises cetyl dimethicone copolyol and polyglyceryl-4-isosterate and hexyl laurate.

45. The method of claim 44 further comprising the step of mixing the cetyl dimethicone copolyol and polyglyceryl-4-isosterate and hexyl laurate in the range of 98-50/1-40/1-10 percent by weight respectively.

46. A method of studying changes in the skin surface caused by substances applied to the skin by making a before and after positive skin surface replica casting of the skin surface test area comprising the steps of:
mixing a silicone polysiloxane base and a biocompatible surface tension modifying agent;
removing air bubbles from the silicone polysiloxane base and the biocompatible surface tension modifying agent;
marking the skin surface test area;
forming a negative skin surface replica composition comprising a curing catalyst and the silicone polysiloxane base and the biocompatible surface tension modifying agent mixture;
applying the negative skin surface replica composition to the skin surface area to be replicated;
curing the negative skin surface replica composition;
forming a negative surface replica casting from the cured negative surface replica composition;
removing the negative skin surface replica casting from the skin surface area;
placing the negative skin surface replica casting replicated surface side up in a container;
forming a positive skin surface replica composition comprising a polyethylene, a polyethylene copolymer and a pigment;
heating the positive skin surface replica composition;
covering the negative skin surface replica casting with the heated positive skin surface replica composition;
centrifuging the container;
cooling the container;
forming a positive surface replica casting from the negative surface replica casting and the cooled liquid surface replica composition;
separating a connected positive and negative skin surface replica castings at the interface;
applying a test substance on the skin surface test area;
preparing a second negative skin surface replica casting of the test area;
preparing a second positive skin surface replica casting of the test area;
comparing the first and second positive skin surface replica castings;
wherein the biocompatible surface tension modifying agent comprises a mixture of a surfactant and at least one non-ionic emulsifier; and
wherein the surfactant and at least one non-ionic emulsifier mixture comprises cetyl dimethicone copolyol and polyglyceryl-3-oleate and hexyl laurate.

47. The method of claim 46 further comprising the step of mixing cetyl dimethicone and polyglyceryl-3-oleate and hexyl laurate in the range of 98-50/1-40-/1-10 percent by weight respectively.

48. The method of claim 33 wherein the biocompatible surface tension modifying agent comprises from 0.10% to 5.0% by weight of the total weight of the negative skin surface replica composition based on a 100 gram batch minimum.

49. The method of claim 40 wherein the surfactant and non-ionic emulsifier mixture comprises from 0.10% to 5.0% by weight of the total weight of the negative skin surface replica composition based on a 100 gram batch minimum.

50. The method of claim 33 wherein the biocompatible surface tension modifying agent comprises 0.75% by weight of the total weight of the negative skin surface replica composition based on a 100 gram batch minimum.

51. The method of claim 40 wherein the surfactant and at least one non-ionic emulsifier mixture comprises 0.75% by weight of the total weight of the negative skin surface replica composition based on a 100 gram batch minimum.

52. The method of claim 33 wherein the curing catalyst is a metallic salt of carboxylic acid.

53. The method of claim 52 wherein the metallic salt of carboxylic acid is stannous tin octoate.

54. The method of claim 53 wherein the stannous tin octoate comprises 2.0% to 5.0% by weight of the total weight of the silicone polysiloxane base and biocompatible surface tension modifying agent mixture.

55. The method of claim 53 wherein the stannous tin octoate comprises 2.5% by weight of the total weight of the silicone polysiloxane base and biocompatible surface tension modifying agent mixture.

56. The method of claim 33 wherein the curing catalyst comprises 2.0% to 5.0% by weight of the silicone polysiloxane base and biocompatible surface tension modifying agent mixture.

57. The method of claim 33 further comprising the step of applying the negative surface replica composition to the surface testing area in a thickness ranging from 2 mm-3 mm.

58. The method of claim 33 further comprising the step of centrifuging the container at 2,000-6,000 RPM.

59. The method of claim 44 further comprising the step of positioning an adhesive collar over the skin surface test area to be replicated.

60. The method of claim 59 further comprising the step of applying the negative skin surface replica composition to the skin surface test area to be replicated and to an inner and an outer ring of the adhesive collar.

61. The method of claim 60 further comprising the step of removing a negative skin surface replica casting and the adhesive collar from the skin surface test area.

62. The method of claim 61 further comprising the step of separating the negative skin surface replica casting from the outer ring of the adhesive collar.

63. The method of claim 44 further comprising the step of cooling the container to room temperature.

64. The method of claim 44 further comprising the step of comparing the first and second positive skin surface replica castings through a magnifying device.

65. The method of claim 44 further comprising the step of mixing the curing catalyst and the silicone polysiloxane base and biocompatible surface tension modifying agent for 8-15 seconds.

66. The method of claim 44 wherein the biocompatible surface tension modifying agent comprises from 0.10% to 5.0% by weight of the total weight of the negative skin surface replica composition based on a 100 gram batch minimum.

67. The method of claim 44 wherein the biocompatible surface tension modifying agent comprises 0.75% by weight of the total weight of the negative skin surface replica composition based on a 100 gram batch minimum.

68. The method of claim 44 wherein the curing catalyst is a metallic salt of carboxylic acid.

69. The method of claim 68 wherein the metallic salt of carboxylic acid is stannous tin octoate.

70. The method of claim 69 wherein the stannous tin octoate comprises 2.0% to 5.0% by weight of the total weight of the silicone polysiloxane base and biocompatible surface tension modifying agent mixture.

71. The method of claim 69 wherein the stannous tin octoate comprises 2.5% by weight of the total weight of the silicone polysiloxane base and biocompatible surface tension modifying agent mixture.

72. The method of claim 44 wherein the curing catalyst comprises 2.0% to 5.0% by weight of the silicone polysiloxane base and biocompatible surface tension modifying agent mixture.

73. The method of claim 44 further comprising the step of applying the negative surface replica composition to the surface area to be replicated in a thickness ranging from 2 mm-3 mm.

74. The method of claim 44 further comprising the step of centrifuging the container at 2,000-6,000 RPM.

* * * * *